US009585913B2

(12) United States Patent
Mitzner et al.

(10) Patent No.: US 9,585,913 B2
(45) Date of Patent: Mar. 7, 2017

(54) CLAY MINERAL FOR REDUCING INORGANIC PHOSPHATES, IN PARTICULAR IN RENAL REPLACEMENT THERAPY

(71) Applicant: Fraunhofer-Gesellschaft zur Forderung der angewandten Forschung e.V., Munich (DE)

(72) Inventors: Steffen Mitzner, Rostock (DE); Claus Kerkhoff, Munster (DE); Frank Emmrich, Leipzig (DE); Anne Breitruck, Rostock (DE); Peggy Bodammer, Rostock (DE); Gerd Kruger, Berlin (DE); Rainer Dallwig, Potsdam (DE)

(73) Assignee: Fraunhofer-Gesellschaft zur Förderung der angewandten Furschung e.V., München (DE)

( * ) Notice: Subject to any disclaimer, the term of this patent is extended or adjusted under 35 U.S.C. 154(b) by 0 days.

(21) Appl. No.: 14/405,734

(22) PCT Filed: May 31, 2013

(86) PCT No.: PCT/EP2013/061255
§ 371 (c)(1),
(2) Date: Apr. 22, 2015

(87) PCT Pub. No.: WO2013/182485
PCT Pub. Date: Dec. 12, 2013

(65) Prior Publication Data
US 2015/0258138 A1 Sep. 17, 2015

(30) Foreign Application Priority Data
Jun. 4, 2012 (DE) .......................... 10 2012 209 411

(51) Int. Cl.
| *A61K 33/06* | (2006.01) |
|---|---|
| *A61K 45/06* | (2006.01) |
| *A61K 33/12* | (2006.01) |
| *A61K 35/02* | (2015.01) |
| *A61K 9/00* | (2006.01) |
| *A61K 9/14* | (2006.01) |

(52) U.S. Cl.
CPC ............ *A61K 33/06* (2013.01); *A61K 9/0053* (2013.01); *A61K 9/14* (2013.01); *A61K 33/12* (2013.01); *A61K 35/02* (2013.01); *A61K 45/06* (2013.01); *Y10T 428/2982* (2015.01)

(58) Field of Classification Search
CPC ........ A61K 33/06; A61K 45/06; A61K 33/12; A61K 35/02; A61K 9/0053; A61K 9/14; Y10T 428/2982
See application file for complete search history.

(56) References Cited

U.S. PATENT DOCUMENTS

| 3,677,939 | A | 7/1972 | Patil et al. | |
|---|---|---|---|---|
| 4,931,289 | A | 6/1990 | Suzuki et al. | |
| 2005/0079135 | A1 | 4/2005 | Haslam et al. | |
| 2008/0008763 | A1* | 1/2008 | Phillips ................ | A61K 31/366 424/489 |
| 2008/0026079 | A1 | 1/2008 | Carpenter et al. | |
| 2008/0063697 | A1 | 3/2008 | Bedard | |
| 2009/0017129 | A1* | 1/2009 | Ma'or ................... | A61K 8/965 424/600 |
| 2010/0004588 | A1 | 1/2010 | Yeh et al. | |
| 2010/0215770 | A1 | 8/2010 | Newton et al. | |
| 2010/0272769 | A1* | 10/2010 | Darlington, Jr. ....... | A01N 59/00 424/409 |
| 2012/0003328 | A1 | 1/2012 | Zheng et al. | |
| 2012/0058157 | A1 | 3/2012 | Darlington, Jr. | |

FOREIGN PATENT DOCUMENTS

| CN | 000001720924 A | | 1/2006 | |
|---|---|---|---|---|
| CN | 101347454 A | | 1/2009 | |
| DE | 4446122 A1 | | 6/1996 | |
| EP | 1270001 A1 | | 1/2003 | |
| EP | 2380850 A1 | | 10/2011 | |
| GB | WO2009/050468 | * | 4/2009 | ............ A61K 33/26 |
| JP | 2008303189 A | | 12/2008 | |
| WO | 2005018651 A1 | | 3/2005 | |
| WO | 2008013630 A2 | | 1/2008 | |
| WO | 2008030947 A2 | | 3/2008 | |
| WO | 2009050468 A1 | | 4/2009 | |

OTHER PUBLICATIONS

Edzwald et al., Phosphate Adsorption Reactions with Clay Minerals, Environmental Science & Technology, May 1976, pp. 485-490, vol. 10, No. 5.
Grabherr et al., Effect of several doses of zeolite A on feed intake, energy metabolism and on mineral metabolism in dairy cows around calving, Journal of Animal Physiology and Animal Nutrition, Mar. 31, 2008, pp. 221-236, vol. 93.
Obialo, C.I. et al., Clay Pica Has No Hematologic or Metabolic Correlate in Chronic Hemodialysis Patients, Journal of Renal Nutrition, Jan. 2001, pp. 32-36, vol. 11, No. 1.
Hein, R.L., Tonerde als Arznei, Die Welt, Oct. 16, 2008, 1 page.

* cited by examiner

*Primary Examiner* — Sean Basquill
(74) *Attorney, Agent, or Firm* — The Webb Law Firm

(57) ABSTRACT

The invention relates to a clay mineral for use as an agent for reducing the concentration of inorganic phosphate in liquids, in particular in bodily fluids or dialysis liquids, in order to treat hyperphosphatemia, in particular in a renal replacement therapy, wherein before use, the clay mineral is thermally treated at a temperature between 400° C. and 800° C., preferably between 500° C. and 700° C., in particular preferably at 550° C., over a time period of 60 min to 240 min, preferably 90 min to 180 min, in particular preferably 120 min.

20 Claims, 3 Drawing Sheets

CLAY MINERAL FOR REDUCING INORGANIC PHOSPHATES, IN PARTICULAR IN RENAL REPLACEMENT THERAPY

CROSS-REFERENCE TO RELATED APPLICATIONS

This application is the United States national phase of International Application No. PCT/EP2013/061255 filed May 31, 2013, and claims priority to German Patent Application No. 10 2012 209 411.3 filed Jun. 4, 2012, the disclosures of which are hereby incorporated in their entirety by reference.

BACKGROUND OF THE INVENTION

Field of the Invention

The present invention relates to a mineral compound for reducing the concentration of inorganic phosphates in bodily fluids and dialysis fluids.

The present invention relates to a mineral compound for reducing the concentration of inorganic phosphates in bodily fluids and dialysis fluids according to claim 1.

Description of Related Art

Phosphates play an important role in human metabolism and are vital for the function of the human organism. Phosphates usually are supplied by the food and reabsorbed in the intestines. Up to 70% of the phosphates ingested with the food are excreted via the kidneys and the urine. The rest is utilized by the organism. In humans with healthy kidneys the amount of phosphate excreted in the urine per day is about 900 mg on average.

When the normal phosphate values in blood are exceeded, however, the low solubility product of calcium phosphate will lead to its deposition in the vascular systems and a related calcification.

In the case of an insufficient excretion capacity of the kidneys such as in the case of the renal insufficiency, phosphate will be concentrated in the organism of the patients in an undesired quantity, so that an elevated phosphate level occurs in the blood (hyperphosphatemia).

Chronic renal insufficiency is characterized by a slow progressive loss of the renal function. Main causes are inflammations and infections of the kidneys, constriction of the efferent urinary tract and congenital renal diseases. In industrial nations, however, there is an increase in type 2 diabetes mellitus and arterial hypertension-induced renal insufficiency. Renal insufficiency can only can be treated by a renal replacement therapy in the form of a lifelong therapy with dialysis or kidney transplantation.

For renal insufficiency patients, the instrumental extracorporeal hemodialysis is a life-sustaining therapy, which in part over many years must take over the excretory function of the kidneys. In Germany, about 78,000 patients are treated with a renal replacement therapy. More than 5 million people worldwide are suffering from the chronic kidney disease. Despite a constant development and improvement of the dialysis technique, dialysis patients exhibit a morbidity and mortality rate significantly above the level of the normal population. The reason are secondary complications in several organ systems due to a progressing accumulation of uremia toxins which are responsible for the increased cardiovascular risk.

Currently, 115 uremia toxins are known, one of which is phosphate. The phosphate from the group including the small-molecular water-soluble uremia toxins is subject to a permanent control, since the chronic renal insufficiency leads to a hyperphospatemia and is a decisive risk factor for mortality. A reduction of the phosphate supply should be achieved by dialysis, a low-phosphate diet and an intake of phosphate-binding drugs. The reduction of the phosphate concentration in the plasma during the dialysis only is insufficient, however, so that a further reduction of the exogenous phosphate supply is necessary.

By means of phosphate elimination by phosphate-binding drugs, the phosphate quantities ingested with the food should be bound in the gastrointestinal tract and prevented from passing over into the blood stream. Established therapeutic agents are aluminum and calcium salts. However, they are characterized by considerable side effects. Deposits of aluminum in the skeletal system and brain lead to severe impairments of the hematopoiesis and of cerebral functions. Due to the development of a hypercalcemia and the rise in calcium phosphate, calcium salts are highly disadvantageous. Sevelamer and lanthanum carbonate (Fosrenol) are recently developed calcium-free and aluminum-free phosphate binders. The most frequent side effects of all four phosphate binders include disorders of the gastrointestinal tract. Fosrenol, for example, like the other clinically used phosphate binders, can cause gastrointestinal disorders such as nausea, vomiting, diarrhea, constipation, abdominal pain, headache, seizures and encephalopathy. Lanthanum also has a long half-life and is concentrated in bones and various tissues, such as teeth, liver, kidneys or brain.

In addition, drug therapy is permanent and thus represents a considerable cost burden for the health system.

Therefore, it is the problem underlying the present invention to provide a compound or composition for reducing the exogenous phosphate supply or for reducing the phosphate content in the plasma, which does not have the above-mentioned disadvantages.

SUMMARY OF THE INVENTION

Correspondingly, there is provided a clay mineral for reducing the concentration of inorganic phosphate in bodily fluids or dialysis fluids. Bodily fluids in particular are considered to be blood, plasma and/or the fluid of the intestinal contents of humans.

According to the invention, the clay mineral used is thermally treated before use at a temperature between 400° C. and 800° C., preferably between 500° C. and 700° C., in particular preferably at 550° C. over a period of 60 min to 240 min, preferably 90 min to 180 min, in particular preferably 120 min.

The thermal treatment of the clay mineral before its use effects a complete dehydration and an elimination of organic carbon and further organic substances possibly contained in the clay mineral. The thermally treated clay mineral surprisingly has an improved phosphate binding capacity as compared to the untreated clay mineral. As compared to the phosphate binders typically used so far, the thermally treated clay mineral has an increased or equivalent phosphate binding capacity, but without its undesired side effects, in particular in the case of an oral administration.

In a particularly preferred embodiment, the clay mineral is suitable for reducing the concentration of inorganic phosphate, in particular in the blood plasma, for the treatment of hyperphosphatemia, in particular within a renal replacement therapy. The clay mineral accordingly can be used for producing a composition for the treatment of hyperphosphatemia.

In the present case, a clay mineral such as in the form of a mineral silicate thus is used as phosphate adsorber. Due to specific properties such as swelling capacity, ion exchange capacity, capacity for thixotropy and adsorption of mycotoxins or lipopolysaccharides (LPS), these minerals offer a wide variety of possible uses in humans and animals.

Corresponding to the present invention it accordingly is provided to take the clay mineral either orally for reducing the exogenous phosphate supply, but also externally, i.e. without oral administration, directly in the dialysis fluid while dialysis is performed for reducing the phosphate content. In the case of an oral administration, the clay mineral also can be used without thermal treatment, i.e. in its original form.

In a further preferred embodiment, the clay mineral is enriched with divalent cations, in particular magnesium ions, before its use after the thermal treatment. Enriching the thermally treated clay mineral with divalent cations, such as magnesium ions, leads to an again improved phosphate binding capacity of the clay mineral. In principle, all divalent cations can be used, wherein care should merely be taken for the tolerance of the divalent cations. It is imaginable, for example, to also use $Ca^{2+}$ or $Fe^{2+}$ ions instead of or in addition to said $Mg^{2+}$ ions.

The content of divalent cation such as $Mg^{2+}$ in the clay mineral can lie in a range between 5 and 20 mass-% (based on the dry clay mineral), preferably between 5 and 15 mass-%, in particular preferably at 10 mass-%. For example, 1 g of clay mineral absorbed with $Mg^{2+}$ includes 100 mg $Mg^{2+}$.

Enriching the clay mineral with divalent cations, such as the magnesium ions, preferably is carried out by using a magnesium salt, in particular magnesium chloride or magnesium sulfate, with a mass percentage between 30 and 70%, preferably between 45 and 60%.

In one embodiment, the used solution containing magnesium ions is prepared by a diaphragmalysis method. In this method, a magnesium chloride solution is split up into an anolyte (chlorine water) and into a catholyte (magnesium water) by an electrolysis. A diaphragm separates both waters from each other. The anolyte is very acid and oxidizes, the catholyte is very basic and reduces. The magnesium solution preferably has a pH value between 7 and 10, in particular of about 9.

In a further preferred embodiment, the thermally treated clay mineral enriched with magnesium ions has a mean particle size of 0.1 to 1 μm, preferably of 0.3 to 0.8 μm, in particular preferably of 0.5 μm. Grinding of the clay mineral can be performed e.g. in an agitator ball mill.

The phosphate binding capacity of the clay mineral thus modified, i.e. of the thermally treated clay mineral enriched with magnesium ions and ground to a mean particle size of 0.4-0.6 μm, is considerably higher than the phosphate binding capacity of the untreated clay mineral (by about the factor of 600) and thus is higher than the phosphate binding capacity of the previously known phosphate binders such as Fosrenol, without having their disadvantages such as gastrointestinal intolerances.

In general, minerals can be divided into 10 different classes, wherein each class as such can again be divided into several different sub-classes. Many minerals have their preferred fields of use. For adsorptive processes, in particular the tectosilicate zeolite and the layered silicate montmorillonite from the silicate group are used. For better comparability of the various montmorillonite qualities the term bentonite was coined, whose mineralogical composition must contain at least 60 to 70% of montmorillonite. For many technical applications, this formation of groups is very helpful. The effect of minerals in biological systems, however, goes far beyond adsorption processes. Therefore, the sole fixation to only one montmorillonite content as high as possible in the mineral compound does not lead to the desired result.

The mineral compounds or matrices frequently occurring in nature, with alternate-layer (mixed-layer) clay minerals as main constituent, more rarely are used for adsorptive and catalytic applications due to their lower measurable specific surface areas, swelling capacities and cation exchange capacities as compared to pure montmorillonite layers.

It has now been found that naturally occurring mineral compounds or matrices of marine genesis consisting of mixed-layer or alternate-layer minerals which are composed of swellable and non-swellable layers in irregular sequence and which possibly also contain other minerals such as silicates, oxides, carbonates, sulfides and sulfates, very well have adsorptive and other interesting properties after a corresponding treatment.

Mixed layers structurally can consist of very different alternate layers, such as kaolinite/smectite, chlorite/vermiculite, mica/vermiculite, or very frequently of alternate layers of illite/smectite or illite/montmorillonite. As a result, a wider variety of exchange reactions of cations and anions are possible than with pure montmorillonites. Mixed layers in a combination with other reactive minerals therefore are particularly useful for binding substances in solution in biological systems.

In one embodiment of the present invention, there is used a clay mineral which comprises at least one alternate-layer clay mineral.

Particularly preferably, there is used an alternate-layer clay mineral of montmorillonite and illite/muscovite, wherein in this alternate-layer mineral montmorillonite and illite/muscovite can be contained in a ratio of 60:40 to 40:60, with a ratio of 50:50 being preferred. This means that montmorillonite and illite/muscovite each can be contained at 50 wt-%.

In addition to the minerals montmorillonite and illite/muscovite the preferably used clay mineral also can include contents of other clay minerals, such as kaolinites and chlorites, carbonates, sulfides, oxides and sulfates.

In a preferred embodiment, the clay mineral has a ratio $Fe^{2+}/Fe^{3+}$ between 0.3 and 1.0, preferably between 0.45 and 1.0. In the present mineral compound, for example, the ratio $Fe^{2+}/Fe^{3+}$ is about 10 times higher than in other known clay minerals and due to this increased ratio $Fe^{2+}/Fe^{3+}$ has a high natural anti-oxidative potential.

In a particularly preferred embodiment, the present clay mineral on average comprises 50-60 wt-%, preferably 55 wt-% of montmorillonite-muscovite alternate layers, 15-25 wt-%, preferably 20 wt-% of illite, 5-9 wt-%, preferably 5 wt-% of kaolinite/chlorite, 10-20 wt-%, preferably 15 wt-% of quartz, 1-2 wt-%, preferably 1 wt-% of calcite, 0.9-1.5 wt-%, preferably 1 wt-% of dolomite, 0.9 to 1.9 wt-%, preferably 1 wt-% of feldspar, 0.9-1.0 wt-%, preferably 1 wt-% of pyrite and 0.6-1.0 wt-%, preferably 1 wt-% of gypsum.

The chemical composition of the main elements can be indicated in wt-% as follows: $SiO_2$ 57.9-59.5; $Al_2O_3$ 17.0-18.5; $Fe_2O_3$ 5.9-7.0; $K_2O$ 2.8-3.5; $MgO$ 1.5-2.6; $Na_2O$ 0.9-1.5; $TiO_2$ 0.6-1.5; $CaO$ 0.25-0.35; $P_2O_5$ 0.09-0.15; others 8.9-10.5.

In the presence of a solvent, a part of the minerals contained in the untreated starting clay mineral passes over into said solvent. A suspension experiment with 2 wt-% of mineral compound in distilled water, wherein the suspension was separated by means of an ultracentrifuge and the supernatant then was analyzed, provided the following results: conductivity 346 µS; pH value 7.3; potassium 5 mg/l; sodium 73 mg/l; chlorine 20 mg/l; magnesium 0 mg/l; calcium 1 mg/l; $SO_4$ 121 mg/l; aluminum 0 mg/l; $SiO_2$ 8 mg/l; iron 0 mg/l.

What should be emphasized particularly is the high content of sulfates and the fact that no aluminum ions go into solution. This is particularly important for the application in humans.

Another particularity of the untreated starting clay mineral is the high content of organic carbon of 0.4 wt-%. Together with the sulfates and sulfides present, this is an important proof for the marine genesis of the mineral compound and at the same time an essential contribution to the effectiveness of the same. The mineral compound preferably includes at least one iron sulfide, in particular amorphous pyrite $FeS_2$, wherein the iron sulfide can be present in the mineral compound in a mass percentage between 0.5% and 5%, preferably between 0.9% and 3.0%.

The untreated clay mineral has a BET surface area of 50-100 $m^2/g$, preferably 55-65 $m^2/g$, in particular preferably 60 $m^2/g$. The inner surface of the preferably used mineral compound thus is relatively small as compared e.g. to the highly swellable montmorillonites.

The BET surface area of the clay mineral could be increased considerably by the individual treatment steps. The thermally treated clay mineral enriched with divalent cations and ground to a particle size between 0.1 and 1.5 µm has a BET surface area of 200 to 600 $m^2/g$, preferably 300 to 500 $m^2/g$, in particular preferably of 400 to 450 $m^2/g$.

The preferably used untreated starting clay mineral is isolated from the clay deposits present in Germany in Mecklenburg-Western Pomerania, more exactly near Friedland in the Eastern part of the Mecklenburg Seenplatte region, and treated.

The preferably used mineral compound has unique properties, as already mentioned above, in which it substantially differs from other mineral matrices such as bentonite or montmorillonite.

The mineral compound used here not only is capable of binding cations in the existing montmorillonite layers, but also of binding anions. The mechanism of action of the mineral compound used here therefore is different from bentonites. Anionic substances, for example, particularly well are loosely bound at the breaking edges of the illites/muscovites contained in the mineral compound used. The reason are missing or knocked-out potassium ions, which in the mineral compound ensure a charge equalization. Thus, positive charges are obtained, to which anions can loosely be bound. Since bioactive anions have a relatively high molecular mass and hence diameter, the depressions obtained at the breaking edges are not large enough to realize a firm bond. This can only be achieved with smaller molecules, as is demonstrated by the very high adsorptive power for in particular oxygen-containing molecule anions such as phosphate $PO_4^{3-}$, nitrate $NO_3^-$, nitrite $NO_2^-$ and others. A decisive role also is played here by the $Fe^{2+}$ ions at the breaking edges and by hydrogenated iron oxides (FeO(OH)) from the pyrite oxidation, since the same can act as counterions.

To achieve a rather high binding capacity of the present mineral compound, a microfine comminution is advantageous to create a rather high number of breaking edges. As already mentioned above, the preferred particle size is about 0.1 to 1.5 µm, in particular 0.3 to 0.8 µm, quite particularly preferably about 0.4 to 0.5 µm.

In zeta potential examinations it has also been found that due to the microfine comminution e.g. by means of an opposed jet mill the zeta potential of the mineral compound at pH 7 adjusts to a value between 10 and 100 mV, preferably between 30 and 90 mV, in particular preferably between 45 and 90 mV, which indicates a strong increase of the positive docking points for anions.

The clay mineral used here preferably is obtained in a method with the following steps:
a) comminution of the untreated clay mineral to a mean particle size between 1 and 3 µm, preferably between 1 and 2 µm, in particular preferably between 1.2 and 1.5 µm and drying to a final moisture between 0.05 and 1 mass-%, preferably between 0.1 and 0.5 mass-%, in particular preferably between 0.1 and 0.2 mass-%; and
b) thermal treatment of the comminuted clay mineral at a temperature between 400° C. and 800° C., preferably between 500° C. and 700° C., in particular preferably at 550° C. over a period of 60 min to 240 min, preferably 90 min to 180 min, in particular preferably 120 min.

The starting clay mineral is obtained from raw clay in the form of clay pellets with a size of 10 to 50 mm, preferably 15 to 30 mm, and a moisture of 10 to 50 mass-%, preferably 15 to 30 mass-%. The mean particle size of the clay particles in the clay pellets is 5 to 15 µm, preferably 7 to 12 µm, in particular 9 µm.

The initial comminution of the starting clay mineral according to step a) is effected e.g. in a three-stage impact mill/classifier combination for the simultaneous comminution and gentle drying of the starting clay mineral to the above-mentioned particle size and final moisture. In this method step, enrichment of the clay minerals is effected by separation of functionless minerals by up to 50% and an increase of the water absorption capacity by up to 90%.

In the thermal treatment of the comminuted starting clay mineral succeeding in step b) a thermoactivation of the clay mineral takes place with simultaneous complete dehydration and removal of organic substances from the clay mineral.

In a succeeding method step c), the thermally treated clay mineral is dispersed in a solution containing divalent cations, in particular magnesium ions, by forming a colloidal solution. The pH value of the used magnesium ion solution is 7-10, preferably 9. The concentration of the solution of divalent cations, such as $Mg^{2+}$ ions, preferably is 5 to 10 mass-%, in particular 7 mass-%. The content of divalent cations such as $Mg^{2+}$ in the treated clay mineral then preferably is 10 mass-%, based on the clay mineral dry weight, as already explained above.

The amount of the clay mineral which is dispersed in the solution containing magnesium ions can be about 10 to 50 mass-%, preferably 10 to 30 mass-%, in particular preferably about 15 to 20 mass-%.

In a further step d), the colloidal Mg clay mineral solution preferably is ground to a mean particle size of 0.1 to 1.5 µm, preferably of 0.3 to 0.8 µm, in particular preferably of 0.4 to 0.5 µm. Grinding of the colloidal clay mineral can be effected e.g. by using an agitator ball mill. During grinding, the magnesium ions largely are incorporated into the mineral matrix.

Subsequent to the colloid grinding of the thermally treated clay mineral enriched with divalent cations, in particular magnesium ions, the colloidal clay dispersion can be dried by means of existing drying methods, in particular by a vacuum contact drying method e.g. to a residual moisture of 1 to 10 mass-%, preferably 3 to 8 mass-%, in particular preferably 4 to 5 mass-%.

The present clay mineral accordingly is used in a preferred way in the form of a sterilized mineral suspension which can be sterilized e.g. by means of autoclaving. The clay mineral also can be used in a colloidally dispersed and/or gel-like form, with a 15% suspension being preferred particularly.

The present clay mineral can be taken in the form of a capsule, preferably in a single dose. It is imaginable that the clay mineral can be administered as single dose up to 5 times a day. The daily total amount of the clay mineral taken preferably should be 1 g to 50 g, more preferably 5 g to 30 g, in particular 5 g to 15 g. Correspondingly, the amount of a single dose of clay mineral with a daily total amount of 5-15 g can be 1-3 g. The choice of the amount of clay mineral to be administered is influenced by a multitude of factors and correspondingly is to be adapted individually.

It is, however, also possible to administer the clay mineral in the form of a suspension, e.g. 15%-30% suspension. One variant would be e.g. 5 ml from a squeeze tube up to 3 times a day 1 h after the meal. Here as well, an individual adaptation of the amount of clay mineral to be administered is required.

Depending on the treatment step, the present clay mineral has different maximum phosphate binding capacities $Q_{max}$ [mg/g]. $Q_{max}$ as maximum phosphate binding capacity is calculated from the Langmuir isotherm model. It is a theoretical value which is obtained at a high phosphate load per quantity of adsorber.

The untreated starting clay mineral is characterized e.g. by a maximum phosphate binding capacity of about 0.2 mg/g, which in part can be increased by a multiple by the various treatment steps.

The clay mineral comminuted merely according to method step a) already has a maximum phosphate binding capacity of 2 to 4 mg/g, preferably 3 mg/g, whereas the clay mineral thermally treated according to step b) already has a maximum phosphate binding capacity of 10-30 mg/g, preferably 20 mg/g. The enrichment of the thermally treated clay mineral with divalent cations, such as e.g. magnesium ions, effects a further slight increase of the maximum phosphate binding capacity to 20 to 40 mg/g, preferably 30 mg/g.

After colloid grinding of the thermally treated clay mineral treated with divalent cations, in particular $Mg^{2+}$ ions, according to step d), the maximum phosphate binding capacity is increased to values between 100 and 150 mg/g, preferably to 120 mg/g.

BRIEF DESCRIPTION OF THE DRAWINGS

The present invention will be explained in detail by means of the following exemplary embodiments with reference to the Figures, in which.

DESCRIPTION OF THE INVENTION

In the present case, a muscovite-montmorillonite-illite alternate-layer mineral was examined for its properties as phosphate binder, wherein the clay mineral was exposed to various treatment steps.

The Friedland muscovite-montmorillonite-illite alternate-layer mineral is characterized by a small particle size with a large surface area and swellable single layers of sodium-montmorillonite, which provide the silicate with a high water absorption capacity. At the same time, the elements present in the individual interlayers can easily be exchanged against inorganic and organic substances. This process is reversible and of central importance for the adsorption behavior of the Friedland alternate-layer mineral. An essential advantage of the Friedland silicate as compared to other silicates from other worldwide deposits is the low release of aluminum ions. This could be demonstrated in a study of the Federal Institute for Geosciences and Natural Resources (BGR). One cause for this is the treatment process which does without an acid activation of the clay minerals and hence does not release any aluminum ions. It is only the gentle treatment of the mineral compound that provides for the utilization of the Friedland silicate for health purposes.

In the following examinations, the phosphate binding capacity of the Friedland clay mineral was demonstrated, which previously had been subjected to various treatment processes:

Fl15TP: untreated starting clay mineral with a moisture of 15-25 mass-% and a particle size of about 9 μm Fl5pp: clay mineral comminuted to a mean particle size of 1.4 μm with a final moisture of 0.1 mass-%;

Fl5ppK: thermoactivated Fl5pp (thermal treatment at 550° C. for 120 min),

Fl5ppK-D-MG: dispersion of the Fl5ppK with 15-20 mass-% in a magnesium-catholyte water (pH 9) which has been prepared with a diaphragmalysis method; and Fl0.5ppK-D-MG-KV: colloid grinding of the Fl5ppK-D-MG by means of an agitator ball mill to a mean particle size of 0.5 μm.

For measuring the phosphate binding capacity, the various treated samples of the Friedland clay mineral were incubated with a phosphate solution for one hour. The supernatant obtained subsequently could be examined on the analyzer Cobas Mira with regard to its phosphate concentration.

Figure 1:
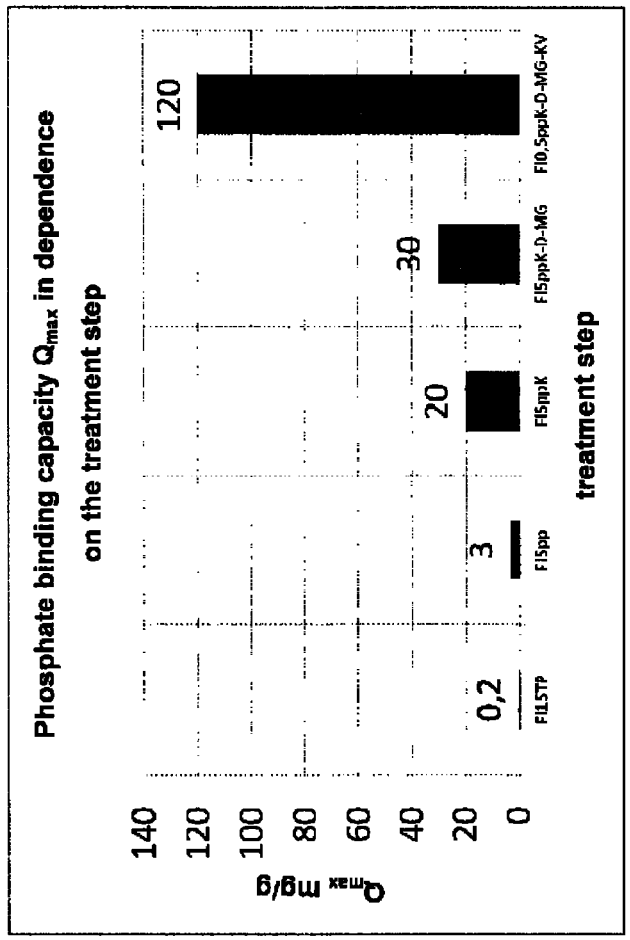
FIG. 1 shows a first diagram for demonstrating the phosphate binding capacity of the clay mineral treated here.
Figure 2:
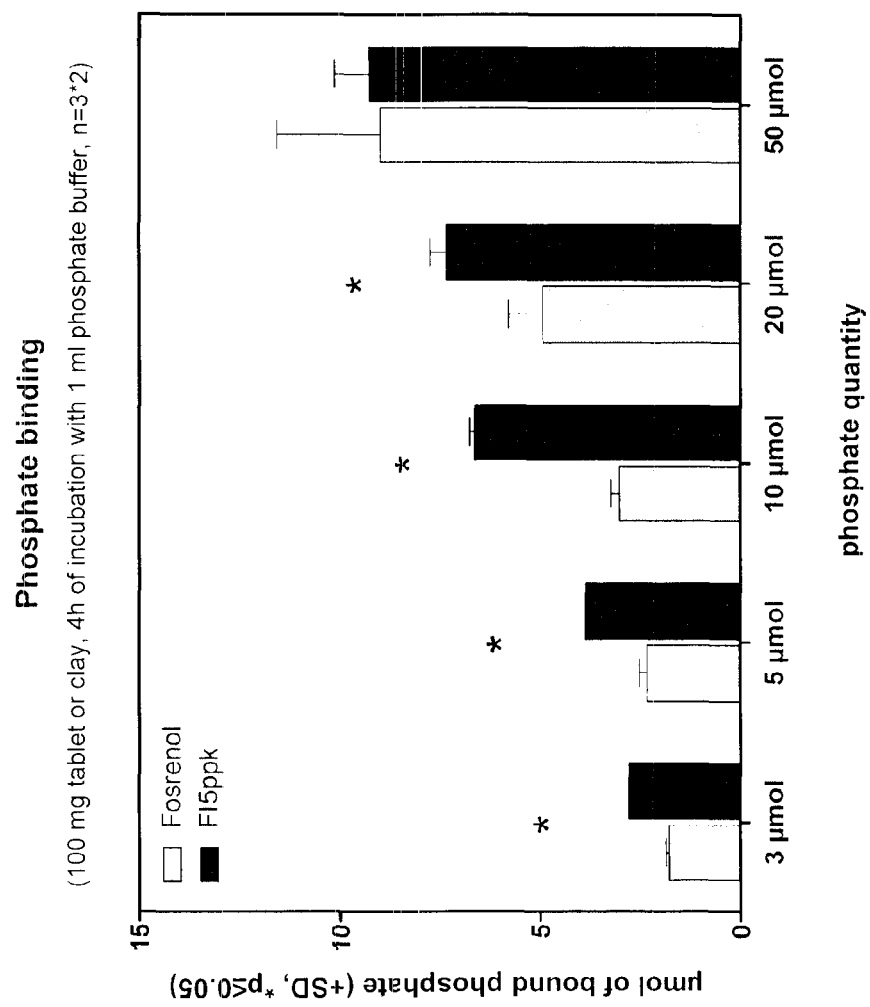
FIG. 2 shows a second diagram for demonstrating the phosphate binding capacity of the thermally treated clay mineral used here in dependence on the phosphate quantity present.

The results show a maximum phosphate binding capacity of the Friedland clay mineral dependent on the pretreatment of the clay mineral (see FIG. 1). The maximum phosphate binding capacity $Q_{max}$ of Fl15TP is 0.2 mg/g, of Fl5pp 3 mg/g, Fl5ppK 20 mg/g, Fl5ppK-D-MG 30 mg/g and Fl0.5ppK-D-MG-KV 120 mg/g.

The maximum phosphate binding capacity is greatly dependent on the present phosphate quantity to be bound. Phosphate binding was determined after 4 h of incubation with 1 ml phosphate buffer. For Fl5ppK increasing phosphate binding was noted with increasing phosphate quantity, but this increase did not occur linearly. The same applies for the comparator product Fosrenol. Interestingly, however, the phosphate binding capacity of Fl5ppK at lower phosphate quantities lies above the binding capacity of Fosrenol and only converges at a phosphate quantity of 50 μmol.

Figure 3:
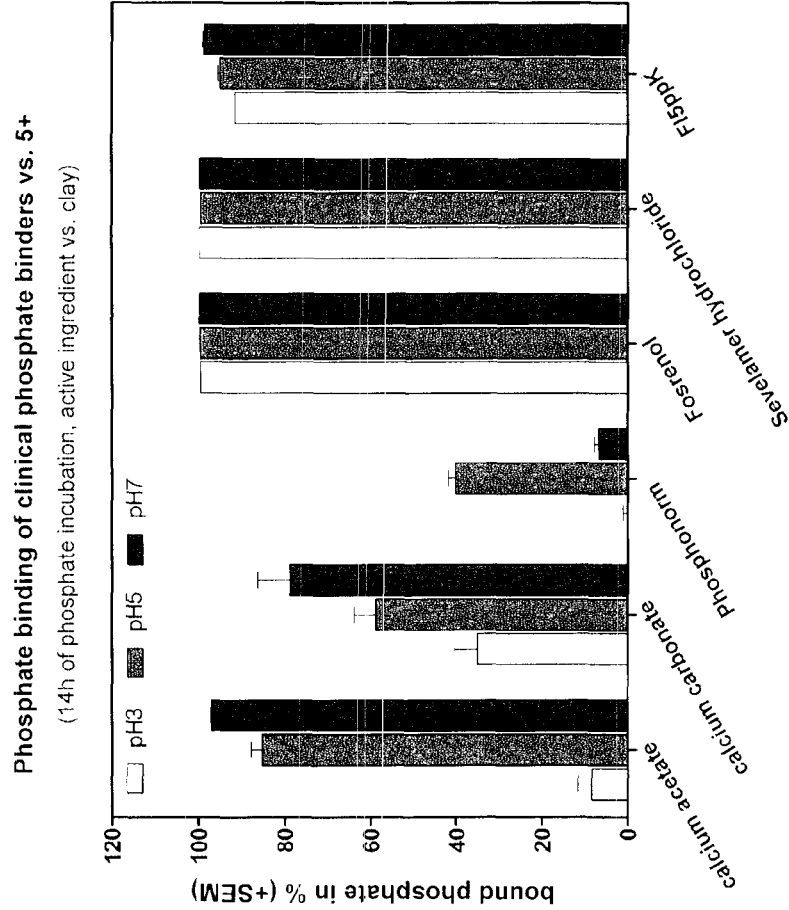
FIG. 3 shows a third diagram for comparison of the phosphate binding capacity of the clay mineral treated here and clinically used phosphate binders.

In the further examinations shown in FIG. 3, the phosphate binding capacity of Fl5ppK was compared with 5 clinically used phosphate binders at different pH values: the calcium-containing phosphate binders calcium acetate and calcium carbonate, Phosphonorm, the calcium-free and aluminum-free phosphate binder Fosrenol, and Sevelamer hydrochloride.

The diagram of FIG. 3 shows the bound phosphate in % after 14 hours of incubation at the pH values 3, 5 and 7.

The phosphate binders calcium acetate, calcium carbonate and Phosphonorm have a strong pH dependence of the phosphate binding capacity, whereas the phosphate binders Fosrenol, Sevelamer hydrochloride and the inventive Fl5ppK are not dependent on the pH value. The phosphate binding capacity of Fl5ppK at the pH values 3, 5 and 7 is at the same level as the phosphate binders Fosrenol and Sevelamer hydrochloride.

The examinations have shown that the thermally treated Friedland clay mineral Fl5ppK has a high phosphate binding capacity which is independent of the pH range. The comparison with commonly used clinical phosphate binders also shows a similar phosphate binding potential.

The present examinations thus have shown that the Friedland clay mineral, in particular in its treated forms, is characterized by high phosphate binding capacities stable in a pH range of 3-8. The comparison with clinically applied phosphate binders revealed that the treated Friedland clay mineral has a comparable phosphate binding capacity based on the quantity of active ingredient. The Friedland clay mineral in addition shows an only low release of aluminum ions.

The Friedland clay mineral, in particular in its treated modifications, is suitable as phosphate binder and can be used in renal insufficiency patients for reducing the exogenous phosphate supply from the food.

The invention claimed is:

1. A silicate clay mineral for use as agent for reducing the concentration of inorganic phosphate in bodily fluids or dialysis fluids for the treatment of hyperphosphatemia, wherein
the silicate clay mineral has a mean particle size of 0.1 to 3 μm and is thermally treated before use at a temperature between 400° C. and 800° C. over a period of 60 min to 240 min.

2. The silicate clay mineral according to claim 1 for reducing the concentration of inorganic phosphate in the blood plasma for the treatment of hyperphosphatemia within a renal replacement therapy.

3. The silicate clay mineral according to claim 1, wherein the silicate clay mineral is enriched with divalent cations.

4. The silicate clay mineral according to claim 3, wherein the enrichment of the silicate clay mineral with magnesium ions is effected by using a magnesium salt with a mass percentage between 30 and 70%.

5. The silicate clay mineral according to claim 1, wherein the silicate clay mineral has a mean particle size of 0.1 to 1.5 μm.

6. The silicate clay mineral according to claim 1, wherein the silicate clay mineral comprises at least one alternate-layer clay mineral.

7. The silicate clay mineral according to claim 1, wherein as alternate-layer clay mineral the silicate clay mineral comprises the clay minerals montmorillonite and illite/muscovite in a ratio of between 60:40 and 40:60, respectively.

8. The silicate clay mineral according to claim 1, wherein further clay minerals are contained.

9. The silicate clay mineral according to claim 1, wherein the silicate clay mineral has a ratio $Fe^{2+}/Fe^{3+}$ between 0.3 and 1.0.

10. The silicate clay mineral according to claim 1, wherein the silicate clay mineral comprises 50-60 wt-% of montmorillonite-muscovite alternate layers, 15-25 wt-% of illite/muscovite, 5-9 wt-% of kaolinite/chlorite, 10-20 wt-% of quartz, 1-2 wt-% of calcite, 0.9-1.5 wt-% of dolomite, 0.9-1.9 wt-% of feldspar, 0.9-2.0 wt-% of pyrite and 0.6-1.0 wt-% of gypsum.

11. The silicate clay mineral according to claim 1, wherein the matrix of the silicate clay mineral has a BET surface area of 50-100 $m^2/g$.

12. The silicate clay mineral according to claim 1, wherein the mineral compound is present in the form of a sterilized mineral suspension.

13. The silicate clay mineral according to claim 1, wherein the mineral compound includes at least one iron sulfide.

14. The silicate clay mineral according to claim 13, wherein the iron sulfide is used in a mass percentage between 0.5% to 5%.

15. A method for reducing the concentration of inorganic phosphate in the bodily fluids of a subject in need thereof, wherein a silicate clay mineral according to claim 1 is taken orally.

16. The silicate clay mineral according to claim 1, wherein the silicate clay mineral is dispersed in a solution to form a colloidal solution and is used in the colloidally dispersed form.

17. A method for producing a silicate clay mineral according to claim 1, comprising the following steps:
    a) comminution of the untreated silicate clay mineral to a mean particle size between 1 and 3 μm and drying to a final moisture between 0.05 and 1 mass-%; and
    b) thermal treatment of the comminuted silicate clay mineral at a temperature between 400° C. and 800° C., over a period of 60 min to 240 min.

18. The method according to claim 17, further including:
c) the thermally treated silicate clay mineral is dispersed in a solution containing magnesium ions by forming a colloidal solution.

19. The method according to claim 18, further including:
d) the colloidal solution is ground to a mean particle size of 0.1 to 1.5 μm.

20. The silicate clay mineral according to claim 16, wherein the silicate clay mineral is dispersed in the colloidally dispersed form as a 15% suspension.

* * * * *